(12) United States Patent
Shoenfeld

(10) Patent No.: US 6,958,769 B2
(45) Date of Patent: Oct. 25, 2005

(54) HIGH RESOLUTION SHEET METAL SCANNER WITH INDEPENDENT TRACKING LIGHT SOURCE

(75) Inventor: Norman A. Shoenfeld, Livingston, NJ (US)

(73) Assignee: S&S X-Ray Products, Inc., Brooklyn, NY (US)

(*) Notice: Subject to any disclaimer, the term of this patent is extended or adjusted under 35 U.S.C. 154(b) by 721 days.

(21) Appl. No.: 10/037,845

(22) Filed: Jan. 7, 2002

(65) Prior Publication Data

US 2002/0057339 A1   May 16, 2002

Related U.S. Application Data

(63) Continuation-in-part of application No. 09/692,239, filed on Oct. 20, 2000, now abandoned.

(51) Int. Cl.[7] .............................................. H04N 7/18
(52) U.S. Cl. ....................... 348/88; 348/125; 348/128; 356/237.1
(58) Field of Search ............................ 348/88, 86, 92, 348/128, 195, 202; 382/141, 149, 152; 356/491, 356/492, 496, 239.1, 239.8, 237.3, 237.6

(56) References Cited

U.S. PATENT DOCUMENTS

| | | | | |
|---|---|---|---|---|
| 4,212,049 A | * | 7/1980 | Maskens | 362/33 |
| 4,417,260 A | * | 11/1983 | Kawai et al. | 347/138 |
| 4,711,579 A | * | 12/1987 | Wilkinson | 356/615 |
| 5,132,791 A | * | 7/1992 | Wertz et al. | 348/88 |
| 5,184,217 A | * | 2/1993 | Doering | 348/88 |
| 5,231,675 A | * | 7/1993 | Sarr et al. | 382/152 |
| 6,236,734 B1 | * | 5/2001 | Barry | 382/100 |

* cited by examiner

Primary Examiner—Gims Philippe
Assistant Examiner—Erick Rekstad
(74) Attorney, Agent, or Firm—Bernhard P. Molldrem, Jr.

(57) ABSTRACT

A high resolution sheet metal scanner employs machine vision to check a sheet metal part or the like for accuracy of punched or drilled holes or other structure. A high-resolution line-scanning camera mounted to an X-Y table, located in an environmentally sealed lower assembly. The sheet metal part is placed upon a transparent support plate. The line-scan camera is precision focused on the top surface of the glass support plate. An elongated linear illuminator is situated above the glass plate. The illuminator extends in the X direction and moves in the Y direction. The camera is transported in the X and Y directions on a carriage of the X-Y table. A computer control may be used for controlling the camera and the X-Y table. The drive for the camera and for the illuminator are mechanically independent.

16 Claims, 3 Drawing Sheets

HIGH RESOLUTION SHEET METAL SCANNER WITH INDEPENDENT TRACKING LIGHT SOURCE

This is a continuation in part of my U.S. Pat. Appln. Ser. No. 09/692,239, filed Oct. 20, 2000, now abandoned.

BACKGROUND OF THE INVENTION

The present invention relates to automatic scanning equipment and techniques, and is more particularly directed to a scanner that employs machine vision to check a sheet metal part or the like for accuracy of punched or drilled holes or other structure. The invention is more specifically concerned with a scanner device and technique in which a metal sheet can be scanned and then compared to an existing drawing or blue-print, which can be in CAD or in digitized form, for ascertaining hole locations and tolerances. The invention is also concerned with scanning devices in which the part can be scanned to produce a blue-print or drawing directly, or on which a blue-print can be scanned using machine vision.

In many manufacturing processes it is necessary to assure the accuracy of dimensions of parts and subassemblies prior to further assembly, and this is particularly true for workpieces or parts that are formed of sheet metal, where holes and cutouts must be in precise locations and must be specific sizes and shapes, within very narrow tolerances.

An automated scanning device is used for this purpose, in which the part to be checked is illuminated and a video image is processed to obtain the required measurement data. In many cases, a laser beam or plural laser beams are swept across the part, and the device picks up either the light reflected from the part or the light that passes through it. In either case, the laser has to be oriented at an angle to the part for capturing portions that are away from the central axis of the scanning device. This produces distortion in images of apertures or of edges, especially if the part has a finite thickness. Other scanning devices employ a video camera that captures an image of the part, or in some cases is moved in an X,Y raster pattern. For these purposes, the part is laid upon a light table, and the camera or other imager is positioned above the light table. In these systems, the camera and the movable carriage are exposed to dust and other atmospheric contaminates that one would expect to find associated with any sheet metal manufacturing process.

OBJECTS AND SUMMARY OF THE INVENTION

Accordingly, it is an object of the present invention to provide an improved technique for optically checking a part for accurate location and tolerance, and which avoids the drawbacks of the prior art.

It is another object to provide a scanner in which any sensitive moving parts are contained within an environmentally sealed housing, so that there are no exposed moving parts.

It is a further object to provide a scanning arrangement which can produce scans of higher resolution or at increased scan speeds.

It is still another object to provide a sheet metal scanner which can accurately measure location and tolerance of holes and openings, even where the part has appreciable thickness.

It is another object to provide a sheet metal scanner which can be adapted for scanning of architectural drawings, blueprints, or the like for conversion into a CAD drawing, a bit-map drawing, or another digital format.

In accordance with an aspect of the present invention, the scanning apparatus is based on a high-resolution, line-scanning camera mounted onto an X-Y table, located in a lower assembly having an environmentally sealed housing. On the top of the housing is a transparent support plate, e.g., a sheet of glass 48 inches by 48 inches, upon which the sheet metal part (or blue-print) is placed. The line-scan camera may be precision focused on the top surface of the glass support plate. Preferably, the focus can be adjusted to levels between the surface and an inch above the surface. Located just above the glass support plate is a light source, i.e., an illuminator, which supplies a line of light across the viewing field. Preferably, the illuminator employs a single high-output fluorescent tube. The illuminator is supported on linear rails and moves in the Y direction, with the tube extending across in the X direction. The drive for the illuminator is separate from the drive for the camera, so the weight and motion of the light source do not affect motion of the camera, and do not cause camera shake. A polarizing filter may optionally be placed in front of (i.e., above) the camera lens to eliminate reflections. In addition to this, inner surfaces of the sealed lower assembly, as well as the surfaces of the X-Y table, may be coated with a non-reflective paint to eliminate light artifacts. In this arrangement, there are no moving parts of the apparatus outside the sealed lower portion, except for the illuminator, so there is little chance of contamination or failure due to factory dust or other particulates on moving parts or on the camera optics. A positioning device allows fine adjustment of the glass support plate to keep the camera in excellent focus for high resolution scans. Also, damping devices can be incorporated into legs of the unit to accommodate for shocks and vibrations. These may be in the form of rubber-based air or oil-filled dampers, and may be tuned to cancel out specific common vibration frequencies on the factory floor.

The X-Y table may be of the type in which there are X- and Y-precision rails, as well as associated lead screws and stepper motors, or timing belts and pulleys and stepper motors, plus motor controllers and high-resolution encoders, permitting high resolution camera movement (e.g., 0.002 inch resolution or better). The size of the scan undertaken by the X-Y table can be controlled to match the size of the part, where the part is smaller than the full 48 by 48 inches, so as to carry out the scan in a reduced time. The camera support on the X- and Y-precision rails has the rails at the level of the camera mounting, so that the camera body sits below the level of the rails. This keeps the center of gravity of the camera below the rails and increases camera stability during movement.

A computer control may be used for controlling the camera and the X-Y table. Software, which may be compatible with Windows NT or Windows 2000, constructs the two-dimensional image of the part from line scans, and may import an existing CAD drawing file for comparison. The CAD file may be in *.DXF or *.DWG format. The software then compares the scan to the drawing. The software compares features on the scanned part to specific features on the drawing, and produces a report regarding which items fall within acceptable tolerance, and which do not. The software may also reverse-engineer a part, creating a *.DXF file or the like based on the scan. The software is also capable of piecing together multiple scans, where an object is greater than 48 inches in length, for example, or may also perform scans of multiple objects placed at the same time on the top surface of the support plate. In the latter case, each object is compared individually with a respective drawing. The software can scan in a high-resolution full phantom for a true calibration over the entire 48-inch-by-48-inch surface. This calibration corrects for slight defects in straightness of the linear rails, sagging of the glass support plate surface, and other factors that can interfere with scan accuracy.

The scan software can be modified for use with commercially available, "off-the-shelf" flat bed scanners which may use a transparency adapter.

The above and many other objects, features, and advantages of this invention will become apparent from the ensuing description of a selected preferred embodiment, which is to be considered in connection with the accompanying Drawing.

DETAILED DESCRIPTION OF THE PREFERRED EMBODIMENT

Figure 1:
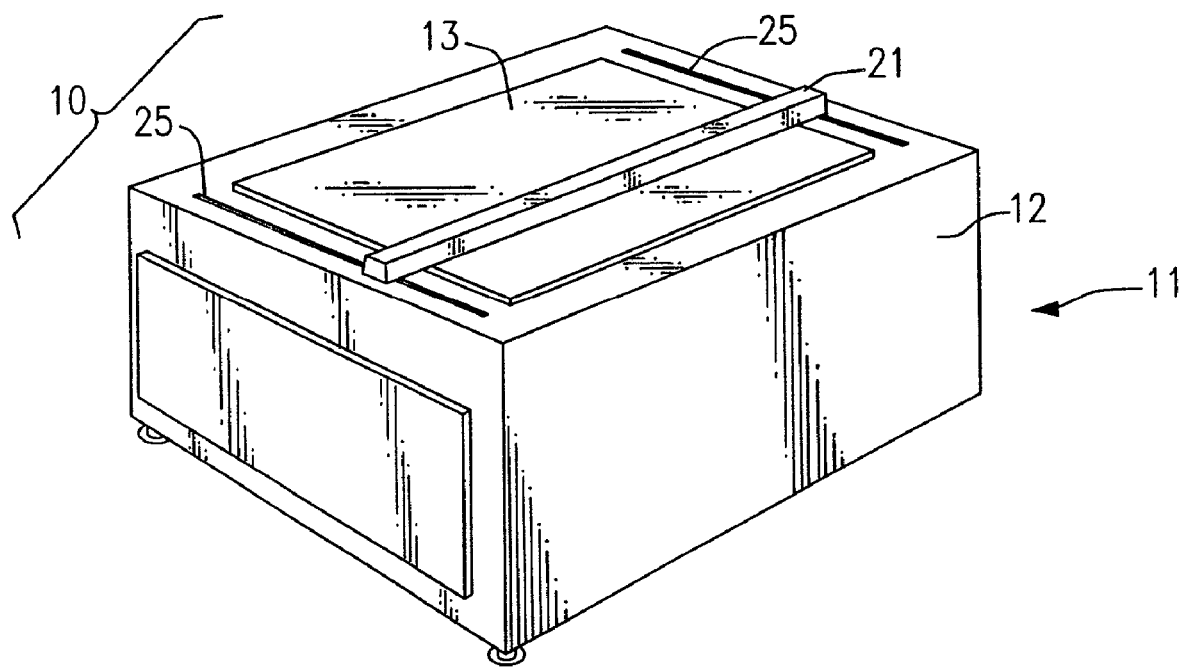
FIG. 1 is a perspective view of a high-resolution sheet metal scanner according to one embodiment of this invention.
Figure 2:
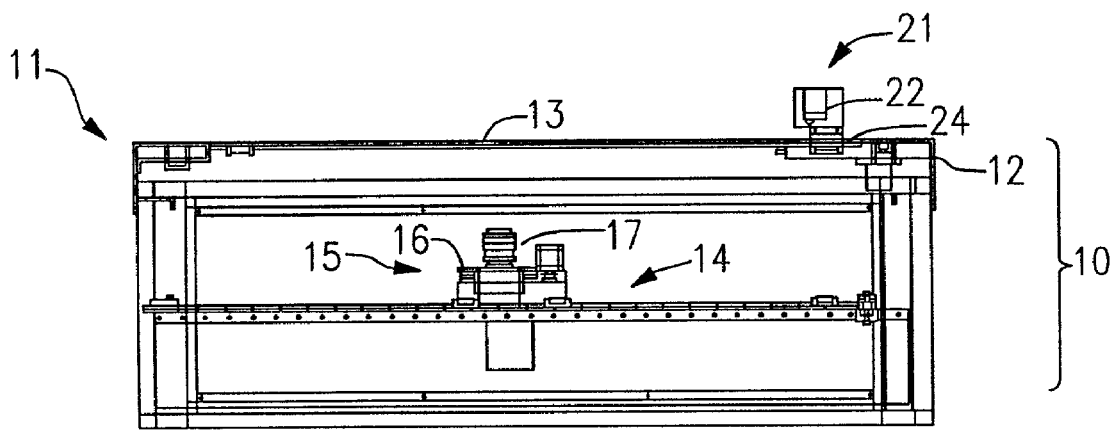
FIG. 2 is a side elevation of this embodiment.

With reference to the Drawing, and initially to FIGS. 1 to 4, a high-resolution scanner arrangement 10 has a lower assembly 11 that is environmentally sealed within a housing 12, with moving parts and all the sensitive optics contained within this sealed housing 12. The lower assembly may be mounted on adjustable support legs. A horizontal flat glass plate 13, here with a width and breadth of 48-inches by 48-inches, and with a thickness of ¾ inch, is fitted into a top wall of the lower assembly 11 and serves as a support plate on which the sheet metal part is laid for checking. A two-stage X-Y table or plotter 14 is situated within the lower assembly housing 12, and has a movable carriage 15 on which a high-resolution line-scan camera 16 is mounted. The camera 16 has its optic axis oriented vertically, and has a focussing lens group 17, and a polarizing filter 18 situated above, i.e., in advance of the lens group 17. The polarizing filter serves to attenuate any stray light that may be, e.g., reflected from the interior surfaces of the lower assembly. Details of the X-Y table 14 will be discussed in more detail later. The interior surfaces of the housing 12, and the surfaces of the X-Y table and other internal elements, are preferably coated with a non-reflective paint which also minimizes any internal reflections.

An elongated illuminator assembly 21 is supported directly above the lower assembly 11, and comprises a housing 22, in which is held a high-output fluorescent tube 23, with a reflector above and a diffuser plate beneath. The diffuser plate may be omitted, if desired. In this embodiment, the illuminator assembly 21 is positioned about one inch above the glass support plate 13, although in other embodiments this distance could be greater or less. Preferably, means are incorporated to adjust the height of the illuminator assembly above the plate 13. The illuminator assembly 22 utilizes high-frequency electronic ballasts for the fluorescent tube 23.

Preferably, there are oil-filled vibration dampers fitted on the legs. These may be adjusted to absorb vibrations at specific frequencies, so as to compensate for vibrations found at the factory floor where the scanner is in use. Other types of vibration dampers and compensators could be employed, including rubber-based or air-filled. These may be tuned by adjusting the pressure or fill. This feature makes the scanner more resistant to normal movement on the factory floor, whereas existing scanners experience difficulties in function or in accuracy, due to shaking and vibrations, when placed in a factory environment. There may be adjustment screws for fine adjustment of the position of the glass support plate 13, such that the image formed by the camera 16 is in sharp focus on the upper surface of the plate 13. This keeps the camera 16 in fine focus for high-resolution scans.

Figure 3:
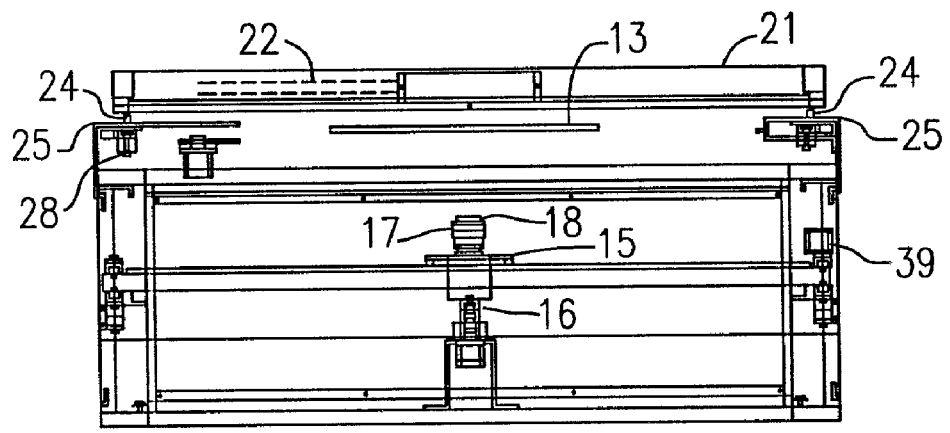
FIG. 3 is a front elevation of this embodiment.
Figure 4:
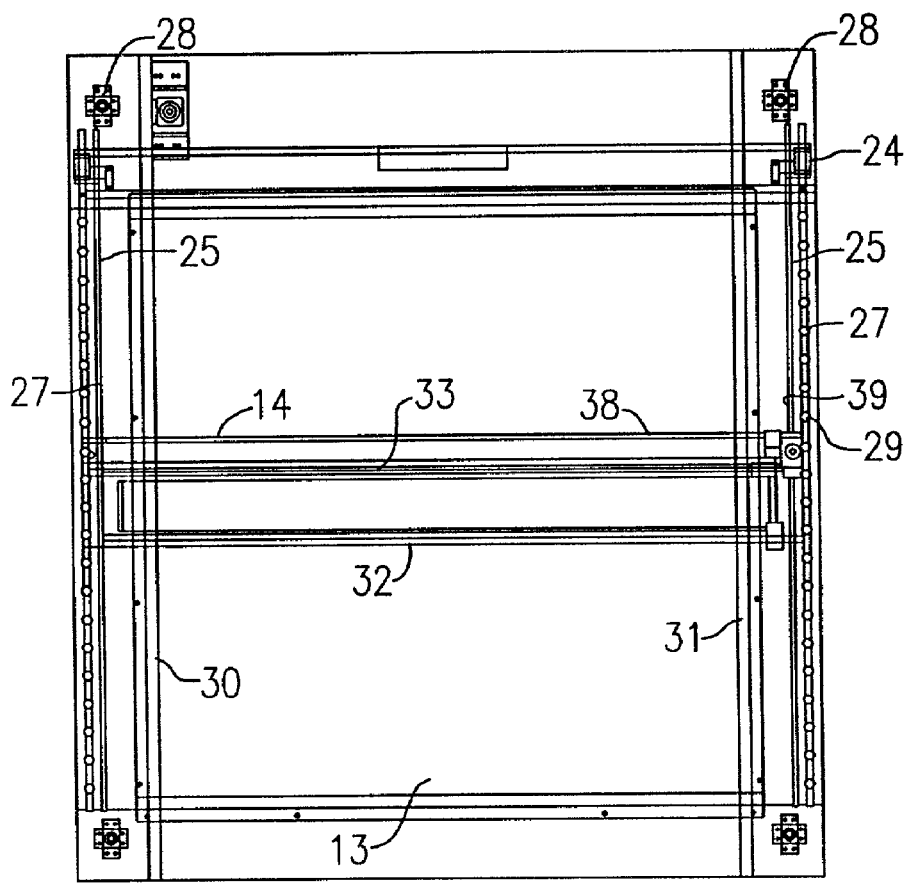
FIG. 4 is a plan view of the lower assembly of this embodiment, taken at 4—4 of FIG. 2.

Details of the X-Y table 14 are shown in FIG. 3, with additional reference to the schematic view of FIG. 4. In this embodiment the table 14 has a pair of first-stage precision rails 30 and 31 that are oriented in the fore-and-aft direction or Y direction. A pair of second-stage precision rails 32 and 33 are movably supported on the rails 30, 31 and these rails 32 are oriented in the orthogonal, i.e., right-to-left or X direction. The carriage 15 is supported on the second stage rails 32, 33. A first stage lead screw 34 (See FIG. 5) is mounted in the housing 12 parallel with the rails 30, 31 and is controllably rotated by a first stage stepper motor 35 to control the position of the second stage rails 32, 33. A second stage lead screw 36 is supported on the rails 33, 34 and parallel with them and is controllably rotated by a second stage stepper motor 37 to control the position of the carriage 15 in the Y direction. As shown here, there are first and second stage encoders 38 and 39 for sensing the position of the table in the X and Y directions, respectively.

The illuminator 21 is supported on its ends by mechanical drive members 24 that project up through slots 25 along the sides of the housing 12. The members 24 are supported on elongated rails 27 and are driven by a stepper motor 28 and a mechanical drive. An encoder 29 senses the position of the illuminator in the Y direction.

All of the moving parts of the X-Y table 14 are contained within the housing 12 and are protected against dust, moisture, and contaminates. The optical elements, i.e., the camera 16, lens group 17 and filter 18, are also environmentally sealed within the lower assembly and thus are also protected from dust and other environmental sources of degradation.

Moreover, in this system, with the camera 16 being vertically oriented and scanned in the X and Y directions against the light of the illuminator 21, which travels in the Y direction in step with the camera, the sheet metal scanner can measure hole positions and dimensions accurately, even for deep, narrow apertures in thick workpieces. The scanning action of this arrangement avoids problems due to parallax, and avoids the elliptical distortion of openings that occurs off-axis with standard camera imaging, especially for parts and workpieces of significant thickness.

Figure 5:
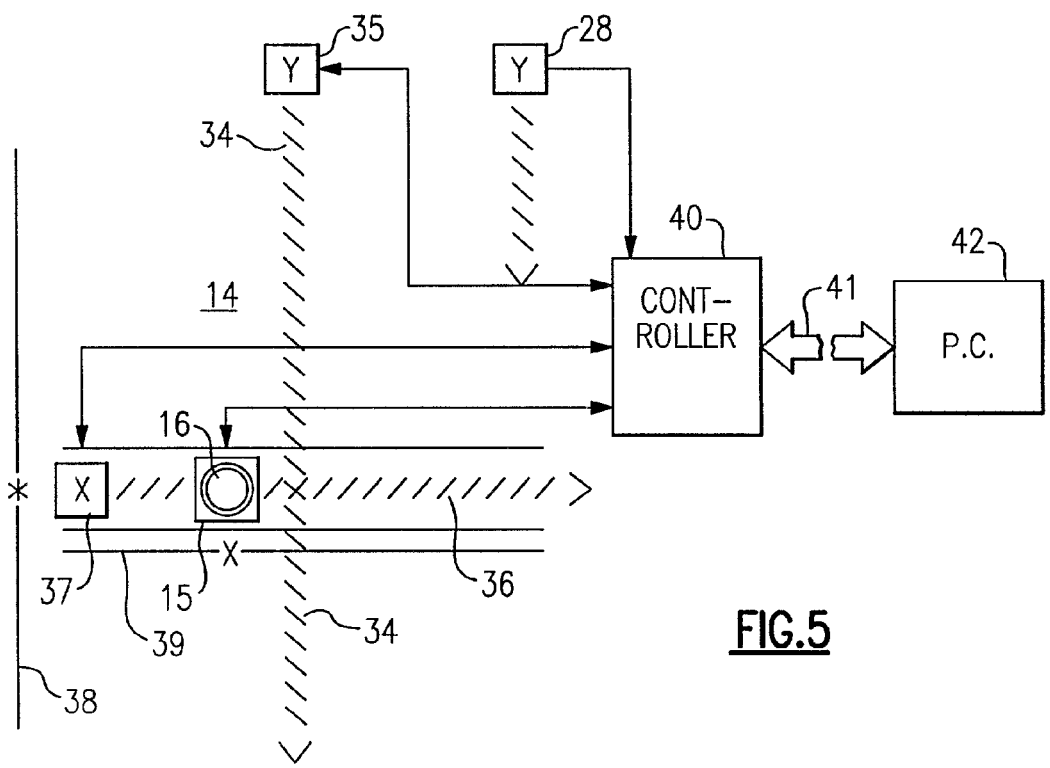
FIG. 5 is a schematic view of this embodiment.

As shown in FIG. 5, in association with the precision encoders, 38, 39, lead screws 34, 36, and stepper motors 35, 37, a controller 40 is provided to control the position of the carriage 15 in the X and Y directions. The controller 40 can be a microprocessor board with leads connecting to the stepper motors 35, and 37, as well as to the encoders 38 and 39. The controller 40 may also include video processing circuitry for storing and/or processing raw lines of video from the camera 16 that is mounted on the X-Y carriage 15. A standard computer cable 41 can link the controller 40 with a computer or PC 42. In the preferred embodiment, the computer 42 has a Windows NT or Windows 2000 operating system, but the invention is not limited to any specific operating system. In other embodiments, the host computer could be a Macintosh or another system. The controller 40 is also coupled to the stepper motor 28 for the illuminator drive. The drive for the camera and the drive for the illuminator are mechanically independent of each other, with the controller 40 tracking the one with the other.

Figure 6:
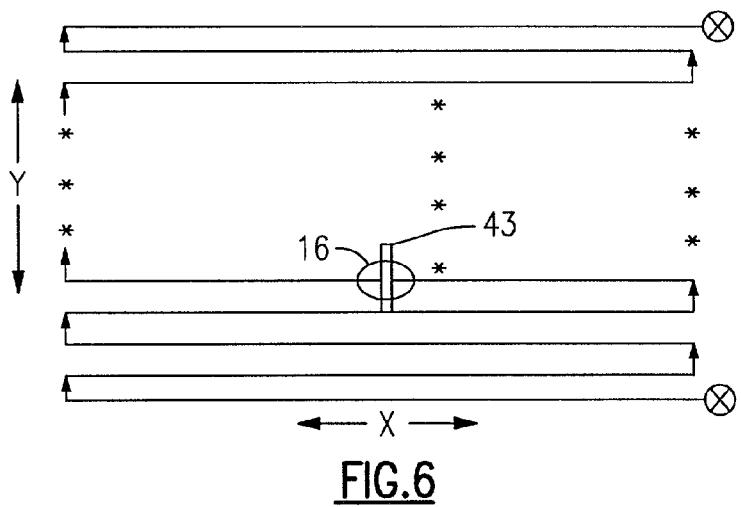
FIG. 6 is a plot of a scan pattern of this embodiment.

As shown in FIG. 6, the X-Y carriage 15 and camera 16 move in a back and forth raster pattern, moving across the scanner in the Y direction, and then moving an increment in the X direction before moving back across in the Y direction. In this case, the line of pixels 43 that is picked up by the camera 16 is oriented horizontally across the scanning or Y direction. There may be some overlap in the scanning from one increment in the X direction to the next. The software used in the computer 42 builds a two-dimensional image based on the pixel lines 43, so that the complete two-dimensional image is accurate to a resolution of 0.002 inches. Of course, it is possible to employ a faster scan if less resolution is needed. The software also makes it possible to piece together multiple partial images, for example, if the part or workpiece has a dimension of more than 48 inches. In addition, if the workpiece is relatively small, i.e., occupying only a fraction of the entire 48-inch square available, then the X-Y table is controlled so as to scan only that portion occupied by the workpiece. The scan size can be entered in terms of X and Y coordinates to match the part size. This produces a faster scan without any loss of resolution.

The associated software can reconstruct a two-dimensional image from the line scans, and can also import an existing CAD drawing file (typically, either in a *.DFX or in a *.DWG format). The software also compares features on the scan to specific features on the drawing, and produces a report regarding which items fall within acceptable tolerance, and which do not. The software can also reverse-engineer a part or workpiece, and can produce a *.DFX file from the scan. This information can be used for producing a blueprint, or for calibrating a machine tool or correcting a calibration. The software permits multiple scans to be pieced together for measuring large objects, and also permits multiple objects all to be placed on the scanning surface of the plate 13 for simultaneous scanning. The objects can later be individually selected from the completed scanned image. The scanned information can also be shared, using network capabilities of the computer 42 and software.

The software also incorporates the capability of calibrating over the entire surface of the support plate, to compensate for defects in the linear rails or in the support plate, so that the image will compensate for any of these errors. Also, the camera includes means for adjusting the focus of the camera to any of several levels at or above the top of the glass support plate 13.

With the illustrated embodiment, it is possible to scan the 48-inch-by-48-inch surface at a resolution of 0.002 inches or better, and it is possible to achieve a scan at a resolution above 0.002 inches in less than two minutes. The scanner 10 can scan objects of an inch, or perhaps more, in thickness, without compromising measurements of aperture size or location.

While the invention has been described hereinabove with reference to a selected preferred embodiment, it should be recognized that the invention is not limited to that precise embodiment. Rather, many modification and variations would present themselves to persons skilled in the art without departing from the scope and spirit of this invention, as defined in the appended claims.

I claim:

1. High-resolution sheet metal scanner using machine vision for checking the accuracy of openings drilled or punched into a mechanical part, comprising:
    a lower assembly which includes a housing; a planar scanning camera carriage assembly within said housing and capable of producing controlled movement of a camera carriage member in two orthogonal directions in a horizontal plane; a flat transparent support plate disposed on an upper side of said housing on which said part is to be supported for viewing; and a camera assembly mounted on said carriage member and oriented upwards including an imager for producing at least one line of pixels and focussing means for focussing said imager upon an upper surface of said support plate;
    a linear illuminator mounted above said lower assembly and providing a substantially uniform light along a line in one of said orthogonal directions, and being linearly movable in the other of said orthogonal directions across said support plate;
    camera carrier control means coupled with said camera carriage assembly and with said camera assembly for guiding said camera assembly in a controlled scanning pattern within said lower assembly housing and processing image data of said part based on pixels produced by said camera assembly imager; and
    illuminator control means for linearly moving said illuminator in the other of said orthogonal directions to track motion of said camera carriage member;
    wherein said linear illuminator is mechanically independent of said camera carriage assembly.

2. The high-resolution sheet metal scanner of claim 1 wherein said camera assembly includes a polarizing filter.

3. The high-resolution sheet metal scanner of claim 1 wherein said illuminator includes a single fluorescent tube extending across said support plate.

4. The high-resolution sheet metal scanner of claim 3 wherein said illuminator is disposed substantially an inch above said support plate.

5. The high-resolution sheet metal scanner of claim 1 wherein said scanning camera carriage assembly includes a first lead screw, a first stepper motor for controllably rotating said first lead screw, a second lead screw, a second stepper motor for controllably rotating the second lead screw, first and second stage rails arranged orthogonally and means for permitting said camera carriage to travel along said first and second stage rails in accordance with rotation of said first and second lead screws.

6. The high-resolution sheet metal scanner of claim 5 including first and second high-resolution encoders within said housing for determining X and Y location of said camera carriage.

7. The high-resolution sheet metal scanner of claim 1 wherein said imager includes a linear imager producing one line of pixels at a time.

8. The high-resolution sheet metal scanner of claim 1 including position adjusting means for fine adjustment of vertical position of said support plate.

9. The high-resolution sheet metal scanner of claim 1 wherein said control means includes means to adjust the dimensions of scan to the size of the part.

10. The high-resolution sheet metal scanner of claim 1 wherein said lower assembly further includes motion damping support means to minimize effects of floor vibration on action of the scanning carriage assembly.

11. The high-resolution sheet metal scanner of claim 10, wherein said motion damping means includes means for tuning to damp out specific frequencies.

12. The high-resolution sheet metal scanner of claim 1, wherein said camera has a body portion with its center of gravity disposed beneath the plane of said scanning camera carriage assembly.

13. The high-resolution sheet metal scanner of claim 1, wherein said camera carrier control means includes means for calibrating over the entire surface of said support plate to compensate for defects in the linear rails and in the support plate.

14. The high-resolution sheet metal scanner of claim 1, further comprising means for adjusting the focussing means of said camera assembly to focus the camera at any of a plurality of different heights above said support plate.

15. The high-resolution sheet metal scanner of claim 1, wherein said housing is environmentally sealed sufficiently to exclude dust and contaminates.

16. The high-resolution sheet metal scanner of claim 4, wherein the height of the illuminator above said support plate is adjustable.

* * * * *